(12) United States Patent
Dusanter et al.

(10) Patent No.: US 10,722,122 B2
(45) Date of Patent: Jul. 28, 2020

(54) DETECTION DEVICE FOR BEDDING FOR SLEEP MONITORING

(71) Applicant: WITHINGS, Issy les Moulineaux (FR)

(72) Inventors: Florent Dusanter, Montrouge (FR); Bastien Rechke, Sevres (FR); Pierre Barrochin, Saint Cloud (FR); Nadine Buard, Meudon (FR); Eric Carreel, Meudon (FR); Lodie Julien, Suresnes (FR)

(73) Assignee: WITHINGS, Issy-les-Moulineaux (FR)

( * ) Notice: Subject to any disclaimer, the term of this patent is extended or adjusted under 35 U.S.C. 154(b) by 580 days.

(21) Appl. No.: 14/546,817

(22) Filed: Nov. 18, 2014

(65) Prior Publication Data

US 2015/0141852 A1    May 21, 2015

(30) Foreign Application Priority Data

Nov. 18, 2013  (FR) ...................... 13 61287

(51) Int. Cl.
*A61B 5/0205* (2006.01)
*A61B 5/11* (2006.01)
(Continued)

(52) U.S. Cl.
CPC .......... *A61B 5/0205* (2013.01); *A61B 5/0022* (2013.01); *A61B 5/08* (2013.01);
(Continued)

(58) Field of Classification Search
CPC ... A61B 5/6892; A61B 5/1102; A61B 5/0205; A61B 5/11; A61B 5/113; A61B 5/024;
(Continued)

(56) References Cited

U.S. PATENT DOCUMENTS 5,744,726 A * 4/1998 Maurer ............... G01L 19/0023
73/724
6,036,660 A * 3/2000 Toms ...................... A61B 5/11
600/534
(Continued)

FOREIGN PATENT DOCUMENTS

| JP | 2007 097996 A | 4/2007 |
| WO | WO 2012/035737 A1 | 3/2012 |
| WO | WO2013/033524 A2 | 3/2013 |

OTHER PUBLICATIONS

Search report for related French Application No. 13 61287; report dated Nov. 18, 2013.

*Primary Examiner* — Christian Jang
*Assistant Examiner* — Karen E Toth
(74) *Attorney, Agent, or Firm* — Miller, Matthias & Hull LLP

(57) ABSTRACT

A detection device, for placement under or on a mattress, configured for the movements of a person lying on the mattress, includes a sensing portion having an inflatable chamber intended to be positioned under the individual, an electronic unit arranged at a distance from the sensing portion and having a pressure sensor, intended to be positioned outside of the bedding, a transmitting portion interposed between the sensing portion and the electronic unit, including a channel establishing a fluid connection between the inflatable chamber and the sensor, the channel having a transverse dimension (T) that is much smaller than the width (L1) of the chamber.

15 Claims, 4 Drawing Sheets

(51) Int. Cl.
*A61B 5/00* (2006.01)
*A61B 5/08* (2006.01)
*A61G 7/05* (2006.01)

(52) U.S. Cl.
CPC .............. *A61B 5/11* (2013.01); *A61B 5/1102* (2013.01); *A61B 5/6892* (2013.01); *A61G 7/05* (2013.01); *A61B 5/0816* (2013.01); *A61B 5/4812* (2013.01); *A61B 2562/168* (2013.01)

(58) Field of Classification Search
CPC ... A61B 5/0816; A61B 5/6891; A61B 5/1126; A61B 5/6887; A61B 5/08; A61B 5/1118; A47C 27/081; A47C 27/083; A47C 27/144

See application file for complete search history.

(56) References Cited

U.S. PATENT DOCUMENTS

| | | | |
|---|---|---|---|
| 2006/0151039 A1* | 7/2006 | Reinhard | F16L 35/00 138/112 |
| 2008/0077020 A1* | 3/2008 | Young | A61B 5/0205 600/484 |
| 2010/0268121 A1* | 10/2010 | Kilborn | A61B 5/412 600/587 |
| 2011/0144455 A1 | 6/2011 | Young et al. | |
| 2011/0271444 A1* | 11/2011 | Davis | A61G 7/1026 5/81.1 R |

* cited by examiner

DETECTION DEVICE FOR BEDDING FOR SLEEP MONITORING

FIELD OF THE DISCLOSURE

The present disclosure relates to detection devices designed to allow sleep monitoring, such detection devices usually being placed in bedding. More specifically, this type of detection device can be installed above a mattress and under a mattress pad or cover; it can also be installed under a mattress topper or below the main mattress or under any other layer; the person to be monitored is intended to be lying down on top of the detection device.

BACKGROUND OF THE DISCLOSURE

The most common devices are formed by a thin inflatable chamber, with a pressure sensor arranged within the chamber to measure pressure variations and thereby deduce information on the heart rate and respiration of the individual lying on the bed.

It is known, for example from document US2011306844, to have a generally square or rectangular air-filled chamber with the pressure sensor arranged in a corner of the chamber. External access to the sensor connector from outside the bedding requires the inflatable chamber to occupy the entire width of the bed so that the connection to the sensor is located at the edge of the bed.

However, it has been found that the performance of chambers of such dimensions is suboptimal in terms of accuracy and sensitivity. In addition, the cost and size of such equipment are quite disadvantageous.

There is therefore a need to provide a more streamlined and less cumbersome solution for helping to monitor the sleep of an individual.

SUMMARY OF THE DISCLOSURE

For this purpose, the disclosure proposes a detection device, intended to be placed on or under a mattress so as to detect by ballistography at least the movements, heart and respiratory rates (by detecting movements or even micromovements) of an individual lying on the mattress, in order to monitor the sleep of the individual, comprising:
a sensing portion comprising at least one inflatable chamber intended to contain a fluid consisting of air, intended to be positioned under the individual, in particular under one of the pressure points of the recumbent individual namely the head, chest, or torso,
an electronic unit arranged at a distance from the sensing portion, comprising at least one pressure sensor, intended to be positioned near the edge of the mattress or bedding,
a transmitting portion, interposed between the sensing portion and the electronic unit, comprising at least one channel (in other words tubing or a fluid link), establishing a fluid connection between the chamber and the sensor so that the electronic unit receives the pressure changes induced by the movements of the individual, no matter how small;
whereby the thickness of the device is very limited under or on the mattress, the only element having a potentially intrusive thickness being arranged outside the bedding (at the edge of the mattress or possibly beyond), and yet the device senses the movements of the individual, no matter how small, in a satisfactory manner with a relatively limited capture surface area, in an optimal manner on the head or torso of the user. The movement detection allows in particular determining the movements, heart rate, and respiratory rate of the individual.

With these arrangements, the sensing surface area is optimal and we avoid having overly large surface areas for the inflatable chamber which are dead volumes for the detection function. With the present disclosure, the dead volumes are smaller so the pressure variations are greater, and it is easier to detect variations.

In embodiments of the device according to the disclosure, one or more of the following arrangements may possibly be used.

The channel of the transmitting portion may have a transverse dimension that is much smaller than the width of the inflatable chamber, whereby the volume of fluid in the transmitting portion is very small and has almost no impact on the measurement.

The detection device may further comprise an air pump and a discharge valve, preferably associated with the electronic unit, the air pump and the discharge valve able to be used by the electronic unit to inflate and/or deflate the sensing portion. It is thus possible to adjust the pressure setpoint using the pump and discharge valve, according to the individual's weight and the weight of the bedding, or even the location of the detection device within the bedding, in particular according to its proximity to the individual. In addition, the system can compensate for possible air loss; also, by associating the pump and discharge valve with the electronic unit, only one housing needs to be installed at the edge of the bedding.

In the inflatable chamber, a plurality of braces are provided, joining at the locations where they are placed the upper and lower walls of the inflatable chamber such that the chamber, even when under pressure, has a thickness that is much smaller than its length and width; whereby one can choose upper and lower walls that are thin or even extremely thin, the strength in the vertical direction being provided by the braces; such that a highly advantageous dimensional insignificance is obtained in terms of thickness while allowing inflation with fluid.

The distance D between the sensing portion and the electronic unit can be greater than 10 cm, whereby the sensing portion can be arranged in the ideal manner under the torso, head, or hips of the user, and the electronic unit can be located outside the actual bedding, preferably against the edge of the bed; in addition, any extra length can be coiled near the electronic unit.

The electronic unit can comprise a module for shaping the sensed signals and a wireless communication module, whereby the electronic unit can make the collected information available to any remote entity such as a base station, a smart phone, and/or a web server, in order to provide the individual or a caregiver with usable information.

The detection device may further comprise a temperature sensor and/or a humidity sensor, so that the movement information can be supplemented with other information relating to the individual's quality of sleep.

When in its deflated state, the device is in the form of a flexible sheet that is foldable, can be rolled up, and is washable. This yields a small volume for the storage and/or delivery of the detection device. It is also possible to wash the detection device with a sponge.

The channel of the transmitting portion comprises a solid flexible rod preventing the complete collapse of the upper wall against the lower wall, so that the fluid communication remains established (and therefore so do the reliable pressure measurements) regardless of the stresses exerted on the transmitting portion. The flexibility of the rod also allows and guides the rolling up of the strip formed by the transmitting portion.

One of the braces is advantageously arranged in alignment with the solid flexible rod at the vicinity of the mouth of the channel into the inflatable chamber; thereby, the rod cannot slide into the inflatable chamber.

The brace which is arranged in alignment with the solid flexible rod comprises a V-shaped end, open toward the solid flexible rod, and is configured to act as a stop for the end of the rod.

The width of the transmitting portion can be substantially the same as the width of the sensing portion. This provides an object that is easy to roll; it also improves its retention within the bedding.

The gas dead volume within the channel of the transmitting portion is minimal, preferably less than 5 cm$^3$, such that the transmitting portion has an almost insignificant influence on performance in the pressure variation detection.

The disclosure also relates to a kit comprising a detection device as described above and a removable slipcover, the detection device being intended for insertion into the slipcover, whereby the slipcover serves as protection and can be washed in a washing machine; in addition, the protective slipcover, because of its rough surface, can fulfill the function of a retaining means for holding in a position corresponding to an optimal position, for example the user's head, chest, or hips.

The disclosure also provides a detection system comprising at least one detection device as described above and a remote entity, whereby an amount of information concerning the quality of sleep is processed and made available to the individual or to a caregiver by a remote entity.

Lastly, the disclosure also provides a method implemented in a device as described above, wherein the electronic unit is configured to adjust, by controlling the air pump and the discharge valve, the pressure prevailing in the inflatable chamber; so that the optimum pressure can be chosen according to the configuration related to the weight of the individual and the position of the device in the bedding, and the type of mattress.

BRIEF DESCRIPTION OF THE DRAWINGS

Other features and advantages of the disclosure will be apparent from the following description of one of its embodiments, given by way of non-limiting example with reference to the accompanying drawings, in which.

DETAILED DESCRIPTION

In the various figures, the same references denote identical or similar elements.

Figure 1:
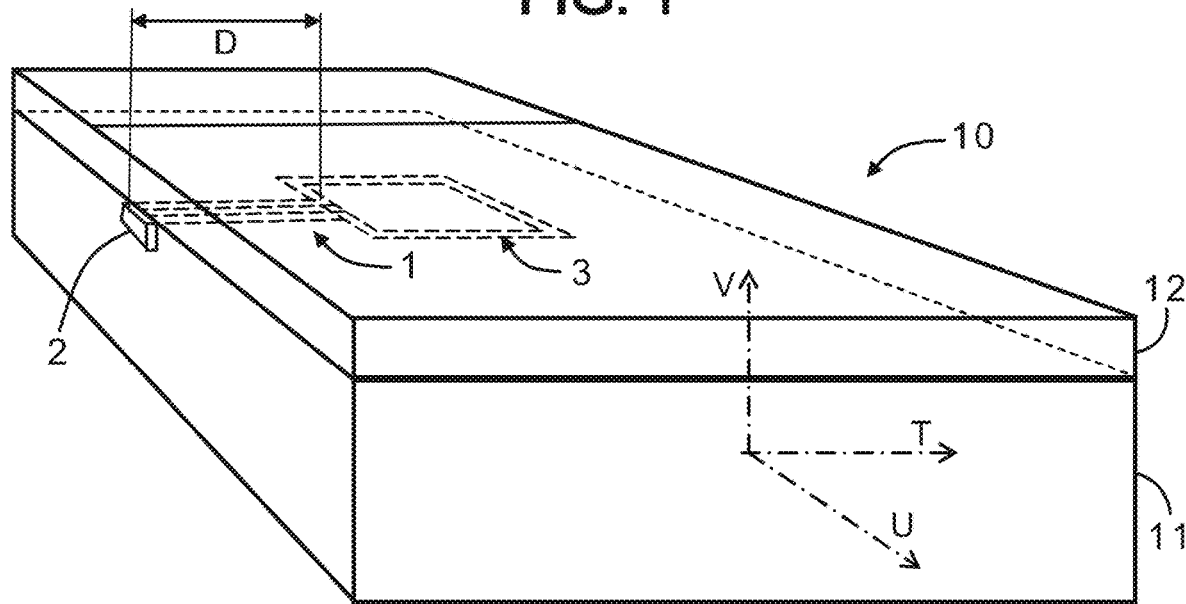
FIG. 1 is a general view of the detection device according to the disclosure, integrated into bedding.
Figure 2:
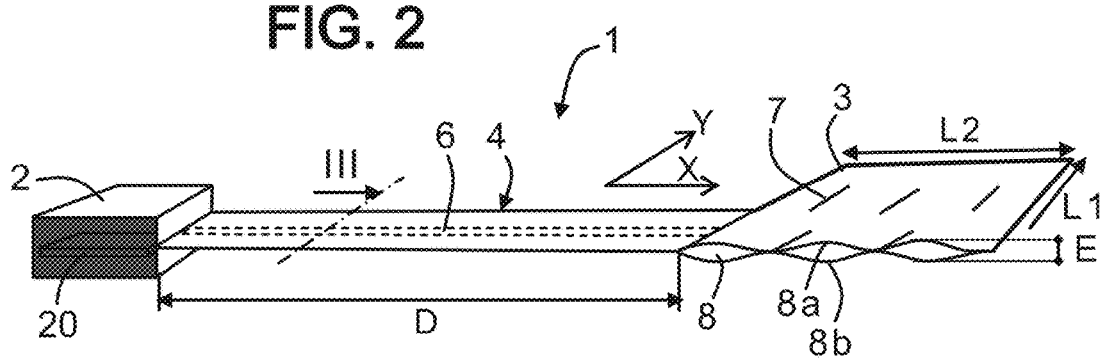
FIG. 2 is an axial sectional perspective view of the detection device of FIG. 1.

FIG. 1 shows an example of bedding 10 according to the present disclosure, which includes a main mattress 11 above which is placed a detection device 1 having an active sensing portion which will be detailed below and for which the position advantageously approximately corresponds to one of the pressure points of the body of the person lying on the mattress. This optimal position can be chosen as the head area, the chest area, the lower torso area (pelvic and hip area). However, any position under the torso or under the head may still be suitable for sufficiently capturing the individual's movements and allow determining by ballistography, from pressure changes induced by the individual's movements, the heart rate and respiratory rate of the individual.

Placed above the detection device 1 is a mattress pad, a mattress topper, a fitted sheet, or other layer 12 on which the individual using the bedding may lie.

In another embodiment not shown, the detection device 1 may be installed under the main mattress.

The detection device 1 is adapted to detect the movements of the user, including movements of very low amplitude, such that an analysis of these small movements allows determining the level of activity, heart rate, and respiratory rate of the individual, even when he or she is laying still. The analysis of detected movements coupled with the heart and respiratory rates allows distinguishing the stages of sleep and recording the individual's various stages of sleep.

In the particular example illustrated in FIGS. 1 to 4, the detection device comprises:
- a sensing portion 3 comprising at least one inflatable chamber 8 intended to contain a fluid, especially gas, particularly air,
- an electronic unit 2, arranged at a distance from the sensing portion, comprising at least one pressure sensor 26 and a circuit board 20,
- a transmitting portion 4, interposed between the sensing portion and the electronic unit, comprising at least one channel 6 establishing a fluid connection between the inflatable chamber and the sensor.

Advantageously, a compressible fluid of high availability is selected for the fluid, in this case ambient air; whereby the sensing portion can be inflated for use, and also the sensing portion can be deflated in order to store the detection device in a compact rolled-up form which will be detailed further below. In addition, using a liquid for the fluid poses the risk of leakage and dampening the bed.

The inflatable chamber 8 occupies most of the sensing portion 3; it has a width L1 (along the Y axis in the drawings), a length L2 (along the X axis in the drawings), and a thickness denoted E in the direction perpendicular to axes X and Y. When the detection device is installed in the bedding, the X and Y axes are located in plane T, U of the bed, and the direction of the thickness E of the inflatable chamber coincides with the vertical direction V.

For the main dimensions of the sensing portion, the width L1 may typically be between 20 cm and 50 cm, and preferably between 30 cm and 40 cm. Similarly, the length L2 may typically be between 20 cm and 50 cm, and preferably between 30 cm and 40 cm. Therefore, the sensing portion does not necessarily occupy the entire width neither of the bed nor of course the entire length of the bed.

The inflatable chamber (in the illustrated example an air chamber) is defined by an upper wall 8a and a lower wall 8b which are welded together along the entire periphery of the chamber. The inflatable chamber advantageously comprises a plurality of braces 7 joining at the locations where they are placed the upper walls 8a and lower walls 8b of the inflatable chamber. Thus, even when under pressure, the inflatable chamber has a thickness E that is much less than its length L2 and its width L1.

When the inflatable chamber is deflated, the thickness E is less than 8 mm, preferably less than 5 mm, more preferably less than 3 mm. It should be noted that a purge valve 90 is provided to allow purging the inflatable chamber.

On one side of the inflatable chamber is a fluid communication with the channel 6 arranged inside the transmitting portion 4.

The channel 6 has a transverse dimension W2 that is much smaller than the width L1 of the chamber, for example between 5 mm and 15 mm.

In the illustrated example, the width W1 of the transmitting portion is also significantly less than the width L1 of the inflatable chamber 8, W1 being for example between 5 cm and 15 cm.

The distance D, corresponding to the length of the transmitting portion along X, separating the sensing portion 3 from the electronic unit 2, is typically greater than 10 cm. Moreover, this distance D can be chosen so that the electronic unit is suspended against the side of the bed, preferably without dragging on the ground, this distance D possibly being for example less than 60 cm.

It should be noted that between the inflatable chamber and the electronic unit, there may be a single channel 6 or two separate channels 6A, 6B whose usefulness will be seen below.

Figure 3:
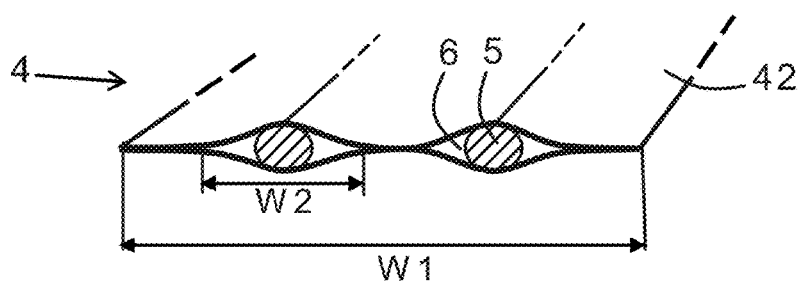
FIG. 3 is a transverse sectional perspective view of the detection device of FIG. 1.

In a preferred aspect, particularly visible in FIG. 3, the transmitting portion 4 comprises a resilient solid rod 5 arranged within the channel 6, to prevent complete collapse of the upper wall against the lower wall of the transmitting portion. This arrangement provides a very small dead volume of fluid in the channel, and at the same time ensures that the fluid communication is maintained regardless of the stresses exerted on the transmitting portion. It is to be noted that the rod 5 is not necessarily solid but can be partially hollow, provided that it is made in a material resistant to crushing but still flexible in flexion mode. The rod had preferably a round cross-section with a diameter chosen between 1 and 3 mm.

Thanks to the presence of this transmitting portion 4, the sensing portion 3 can be positioned at a distance from the electronic unit 2, under the individual, in particular under one of the pressure points of the recumbent individual, namely the head, chest, or lower torso.

Care is taken to minimize the impact of the transmitting portion; in particular the gas dead volume in the channel of the transmitting portion 4 will be minimal, less than 10 cm$^3$, preferably less than 5 cm$^3$ or even less than 2 cm$^3$.

Figure 4:
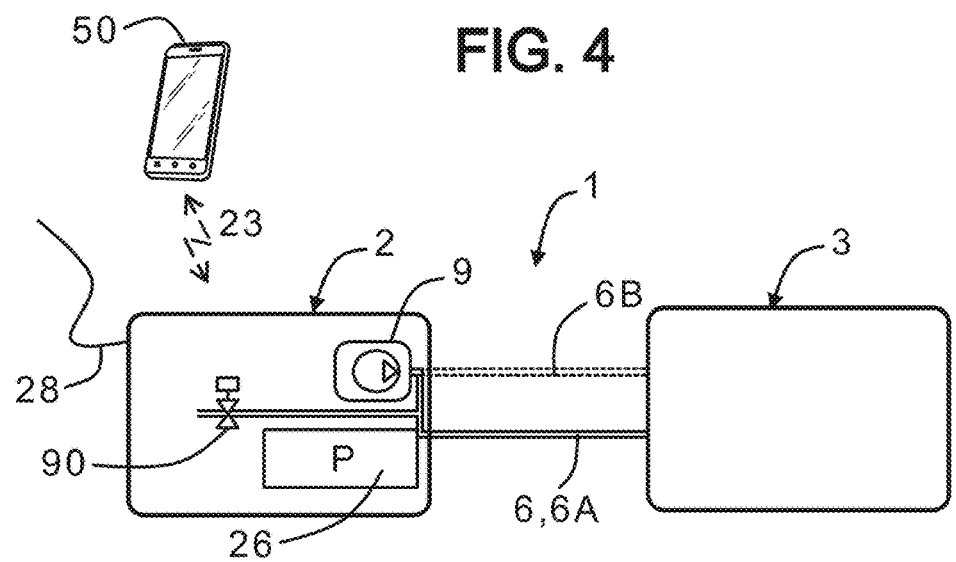
FIG. 4 shows a functional diagram.

As illustrated in FIG. 4, the electronic unit 2 comprises a pressure sensor 26, configured for converting signals of pressure (or pressure variations) into electrical signals that can be shaped and be filtered and analyzed by known means in order to derive the heart rate and respiratory rate of the individual.

In addition, there may be arranged in the electronic unit 2 (or very close to it) an air pump 9 configured to be able to send pressurized air into the channel 6 (6B in the two-channel configuration). Thus the system can compensate for any air losses.

Furthermore, a discharge valve 90 in the form of a solenoid valve may be arranged in the electronic unit 2 (or very close to it). This solenoid valve is controlled so that it is open for a period of time, thereby lowering the pressure in the sensing portion. Activation of the pump and/or discharge valve thus allows adjusting the pressure setpoint according to the weight of the individual, the location of the detection device within the bedding, particularly its proximity to the individual. The farther the detection device is from the individual within the thickness of the bedding, the higher the average pressure setpoint can be.

In addition, when the pump is integrated with the electronic unit 2, there is only one housing to install along the edge of the bedding, which is advantageous in terms of packaging.

The electronic unit may be connected to a power source 28; it may also include a USB communication interface. It may also include a wireless communication means for exchanging data 23 with a remote entity 50, whether a smart phone, computer, tablet, or any other suitable device.

Figure 5:
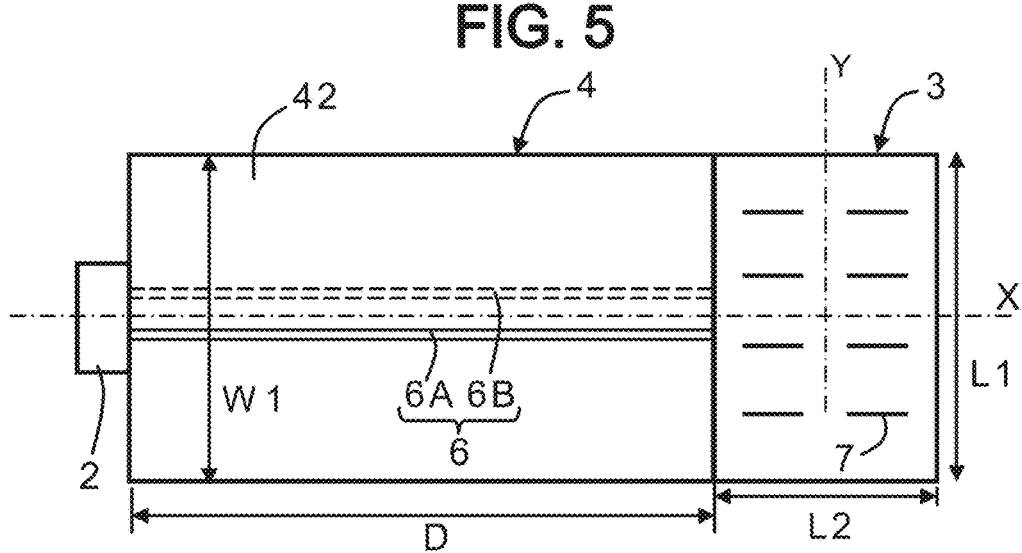
FIG. 5 is a top view of a variant of the detection device, with a wider transmitting portion.
Figure 6:
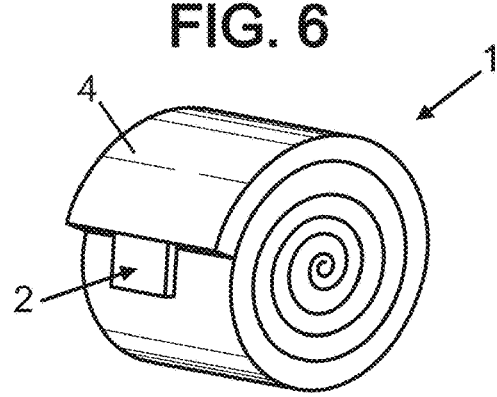
FIG. 6 shows an example of a device according to the disclosure in its delivery or storage configuration, FIGS. 7A and 7B respectively represent configurations for a one-person bed and for a two-person bed.

According to an alternative embodiment shown in FIG. 5, the transmitting portion may have a width W1 that is substantially the same as the width L1 along the Y axis of the sensing portion, which facilitates rolling up the detection device for storage or for its delivery configuration, as is represented in FIG. 6. It should be noted here that the solid rod 5 is sufficiently flexible to allow rolling up the detection device.

According to the disclosure, it is also possible to add to the detection device an optional temperature sensor and/or humidity sensor (not shown), which allows supplementing the sleep quality analysis with information on temperature and sweating.

It is also provided that the detection device, or at least the transmitting portion and sensing portion, can be inserted into a removable slipcover (not shown), to allow washing the slipcover independently of the detection device. In addition, the outer surface of the slipcover may have a certain roughness to prevent the slipcover from sliding relative to the bedding.

Advantageously, this slipcover may be provided with a rough strip for gripping the bedding and contributing to the retention of the detection device in its installed position in the bedding.

It should be noted that, in the configuration represented in FIGS. 3 and 4, the transmitting portion 4 may comprise two separate channels, a first channel 6A forming a pressure measurement channel and a second channel 6B forming a pressurizing channel connected to the pump outlet.

Figure 7A:
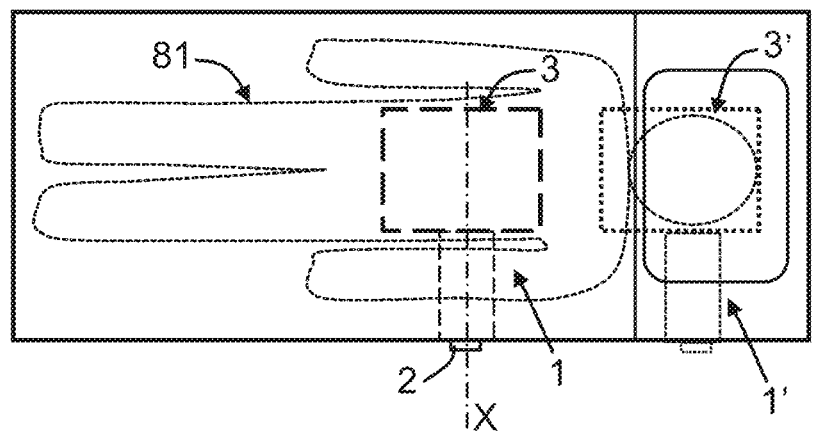
Figure 7B:
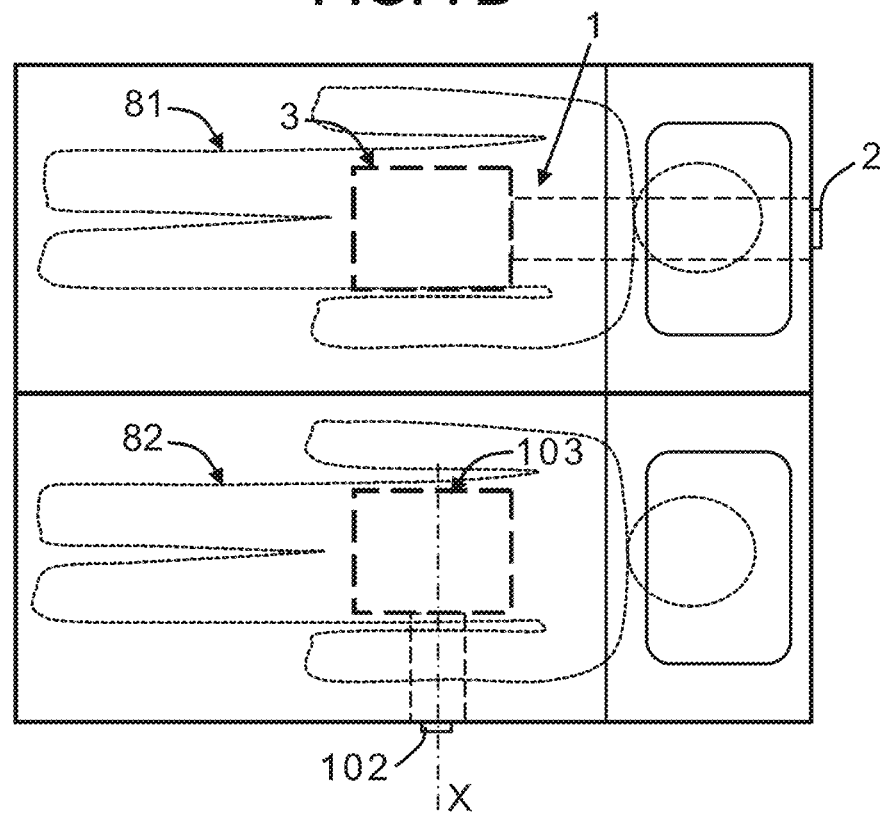

As illustrated in FIGS. 7A and 7B, the electronic unit 2 can be positioned against a lateral side of the bed, or on the headboard side. FIG. 7A illustrates position 3' of the sensing portion under the individual's head, in an alternative placement of the device 1'.

FIG. 7B shows a two-person bed, accommodating two people. In this configuration, a first detection device 1 is placed under the first person and a second detection device 100 is placed under the second person. This second detection device is identical or similar to the first and comprises a sensing portion 103 and an electronic unit 102, the latter being configured to transmit signals representative of the second person's quality of sleep to the remote unit 50.

In this manner, two people can be monitored in a two-person bed through proper targeting of each detection device.

To more accurately sense the various movements of an individual, electrical data from the pressure sensor 26 are analyzed by three parallel paths in the circuit board 20, each having a specific filter, which allows obtaining in the most accurate way possible the individual's heart rate, respiratory rate, and movements during sleep.

Figure 8:
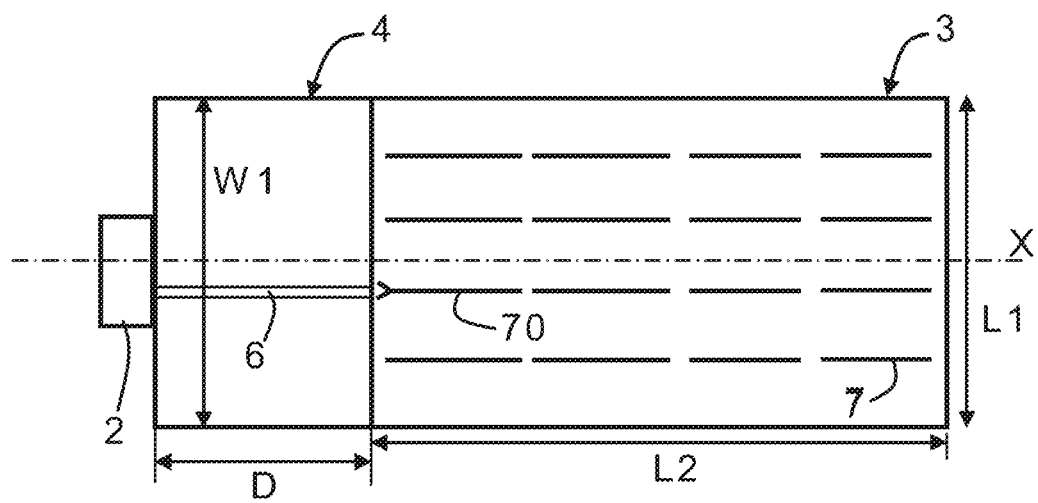
FIG. 8 is similar to FIG. 5 and shows a variant embodiment.

According to a variant embodiment shown at FIG. 8, the dimensions W1 and L1 are similar or identical; the length L2 of the sensing portion 3 is largely greater than the length D of the transmission portion 4. Further, advantageously, one of the brace (referenced 70) is arranged in alignment with the channel 6, and it is therefore located opposite to the end 50 of the solid rod 5 at the vicinity of the mouth of the channel 6 into the inflatable chamber 8.

Figure 9:
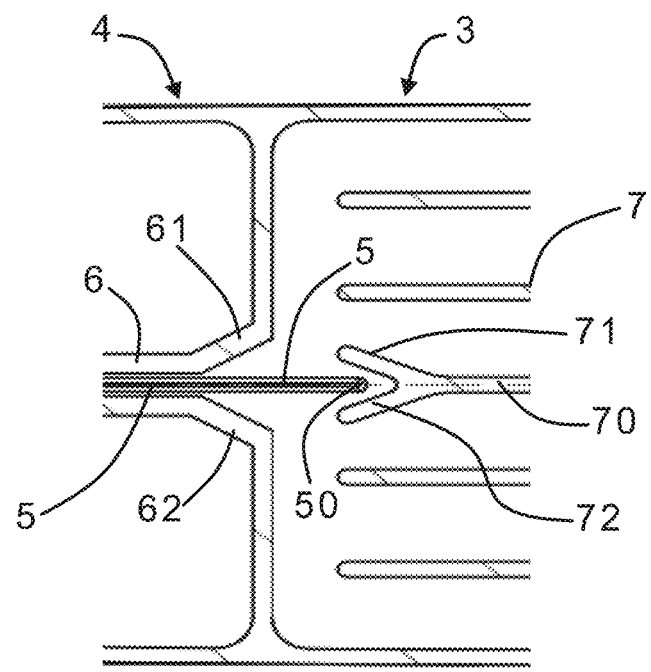
FIG. 9 shows a detail of the interface between the sensing portion and the transmission portion.

As illustrated with more details at FIG. 9, the channel 6 of the transmission portion 4 opens in the inflatable chamber 8 at a tapered mouth 61,62. At the center of the channel 6 is located the above mentioned flexible rod 5 which comprises an end 50 directed toward the inflatable chamber 8.

Since the rod 5 is inserted into the channel 6 without particular fixing, it might move longitudinally (along the X axis) under inflation (or successive inflations) and rolling-ups of the detection device. Advantageously, one of the brace prevents the rod to enter into the inflatable chamber. According to the shown example, the brace referenced 70 extends in the longitudinal axis of the rod 5. Furthermore, the V-shaped end (or Y-shaped) 71,72 opens towards the rod, and thus forms a reliable stop even in case of light misalignment of the rod.

It is noted that even if the braces exhibit a main direction along the Y axis (not shown), the brace which is closest to the channel will act as a stop for the rod possible sliding movement.

The invention claimed is:

1. A detection device, intended to be placed on or under a mattress so as to detect by ballistography at least the movements, heart rates, and respiratory rate of an individual lying on the mattress, in order to monitor the sleep of the individual, comprising:
    a sensing portion comprising at least one inflatable chamber intended to contain a fluid consisting of air, intended to be positioned under the individual, under one of the head, chest, or lower torso of the individual,
    an electronic unit arranged at a distance from the sensing portion, comprising at least one pressure sensor, intended to be positioned externally to the mattress, and
    a pneumatic transmitting portion, distinct from the sensing portion, interposed between the sensing portion and the electronic unit, comprising at least one channel, establishing a fluid connection between the inflatable chamber and the sensor so that the electronic unit receives the pressure changes induced by movements of the individual;
wherein the transmitting portion has upper and lower walls, wherein the channel of the transmitting portion comprises a solid flexible rod preventing the complete collapse of the upper wall of the transmitting portion against the lower wall of the transmitting portion, wherein the inflatable chamber has upper and lower walls, wherein a plurality of braces are provided in the inflatable chamber, joining at the locations where they are placed to the upper and lower walls of the inflatable chamber, and wherein the solid flexible rod extends along and defines a longitudinal axis, and a selected one of the plurality of braces is located at an end of the solid flexible rod and located opposite the solid flexible rod along the same longitudinal axis.

2. The device according to claim 1, further comprising an air pump and a discharge valve associated with the electronic unit, the air pump and the discharge valve able to be used by the electronic unit to inflate and/or deflate the sensing portion.

3. The device according to claim 1, wherein the chamber, even when under pressure, has a thickness that is smaller than its length (L2) and width (L1).

4. The device according to claim 1, wherein the electronic unit comprises a module for converting signals of pressure into electrical signals that can be filtered and analyzed and a wireless communication module configured to send data to a remote entity.

5. The device according to claim 1, further comprising a temperature sensor and/or a humidity sensor.

6. The device according to claim 1, wherein the device in its deflated state is in the form of a flexible sheet that is foldable, can be rolled up, and is washable.

7. The device according to claim 1, wherein the selected one of the plurality of braces which is arranged in alignment with the solid flexible rod comprises a V-shaped end, opened toward the solid flexible rod, and configured to act as a stop for the end of the rod.

8. The device according to claim 1, wherein the width of the transmitting portion is substantially the same as the width along Y of the sensing portion.

9. The device according to claim 1, wherein the gas dead volume within the transmitting portion is less than 10 cm$^3$.

10. A kit comprising a detection device according to claim 1 and a slipcover, the detection device being intended for insertion into the slipcover.

11. A detection system comprising at least one detection device according to claim 1, and a remote entity.

12. A method implemented in a device according to claim 2, wherein the electronic unit is configured to adjust, by controlling the air pump and the discharge valve, the pressure prevailing in the inflatable chamber.

13. The device according to claim 1, wherein the solid flexible rod has a solid convex cross section.

14. The device according to claim 1, wherein the solid flexible rod has a solid round cross section.

15. The device according to claim 1, wherein the distance between the sensing portion and the electronic unit is greater than 10 cm.

* * * * *